(12) United States Patent
Bahia et al.

(10) Patent No.: US 7,047,820 B2
(45) Date of Patent: May 23, 2006

(54) APPARATUS AND METHOD FOR TESTING MATERIAL PERFORMANCE

(75) Inventors: Hussain U. Bahia, Madison, WI (US); Guler Murat, Madison, WI (US); Peter J. Bosscher, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/690,929

(22) Filed: Oct. 22, 2003

(65) Prior Publication Data
US 2004/0177702 A1 Sep. 16, 2004

Related U.S. Application Data

(63) Continuation of application No. 09/803,416, filed on Mar. 9, 2001, now Pat. No. 6,694,823.

(60) Provisional application No. 60/191,535, filed on Mar. 23, 2000.

(51) Int. Cl.
*G01N 3/08* (2006.01)
(52) U.S. Cl. .................................................. 73/819
(58) Field of Classification Search ................ 73/824, 73/818, 795, 819, 841, 862.043, 862.629, 73/862, 451, 862.628, 862.631, 862.042; 177/211
See application file for complete search history.

(56) References Cited

U.S. PATENT DOCUMENTS

| | | | |
|---|---|---|---|
| 2,972,249 A | 2/1961 | McRae et al. | |
| 3,478,572 A | 11/1969 | McRae et al. | |
| 4,177,868 A * | 12/1979 | Sanders et al. | 177/211 |
| 4,502,338 A | 3/1985 | Smith et al. | |
| 4,666,006 A * | 5/1987 | Wernimont | 177/211 |
| 5,036,709 A | 8/1991 | McRae | |
| 5,275,056 A | 1/1994 | Hamilton et al. | |
| 5,291,795 A * | 3/1994 | Hafner | 73/862.629 |
| 5,456,118 A | 10/1995 | Hines et al. | |

(Continued)

OTHER PUBLICATIONS

Bahia et al., "Optimization of Constructibility and Resistance to Traffic: A New Design Approach for HMA Using the Superpave Compactor", *Journal of the Association of Asphalt Paving Technologists*, vol. 67, pp. 189-232 (1998).

(Continued)

*Primary Examiner*—Max Noori
*Assistant Examiner*—Octavia Davis
(74) *Attorney, Agent, or Firm*—Michael Best & Friedrich LLP

(57) ABSTRACT

There is provided an apparatus (LCPA) for measuring a load applied to a quantity of material. The LCPA includes a load cell assembly sandwiched between an inner plate and an outer plate. The load cell assembly measures the load applied to the quantity of material when a force is exerted against the outer plate. Preferably, the load cell assembly includes three equally spaced apart load cells. In one aspect, the LCPA is a part of a gyratory compactor such that the LCPA measures the load applied to a paving material test specimen when a ram exerts a force against the outer plate during the compaction and gyration process. In one aspect, the location of the resultant force exerted by the ram on the specimen is calculated so that the performance of the test specimen may be evaluated. In one aspect, the shear resistance of the specimen is calculated based in part on the location of the resultant force so that a prediction can be made as to whether a particular paving material is suitable for actual field applications.

10 Claims, 12 Drawing Sheets

U.S. PATENT DOCUMENTS

| | | | |
|---|---|---|---|
| 5,606,133 | A | 2/1997 | Hines et al. |
| 5,817,946 | A | 10/1998 | Brovold |
| 5,824,913 | A | 10/1998 | Pyle |
| 5,911,164 | A | 6/1999 | McRae |
| 5,916,504 | A | 6/1999 | Edwards, Jr. et al. |
| 5,939,642 | A | 8/1999 | King et al. |
| 6,026,692 | A * | 2/2000 | Brovold .................. 73/818 |
| 6,205,864 | B1 | 3/2001 | Vialletel et al. |
| 6,354,155 | B1 * | 3/2002 | Berme ............... 73/862.043 |
| 6,532,830 | B1 * | 3/2003 | Jansen et al. ......... 73/862.042 |
| 6,694,823 | B1 * | 2/2004 | Bahia et al. ................. 73/818 |
| 2001/0049969 | A1 | 12/2001 | Bahai et al. |

OTHER PUBLICATIONS

Brown, E.R. and Mallick, Rajib B., "An Initial Evaluation for $N_{design}$ Superpave Gyratory Compactor", *Journal of the Association of Asphalt Paving Technologists*, vol. 67, pp. 101-124 (1998).

Anderson, R. Michael and Hussain, U. Bahia, "Evaluation and Selection of Aggregate Gradations for Asphalt Mixtures Using Superpave", *TRR*, 1583, pp. 91-97 (1997).

RILEM, Bituminous Binders and Mixes, *Report of RILEM Technical Committee 152-PBM Performance of Bituminous Materials*, RILEM, NY 10001 (1998).

Butcher, M., "Determining Gyratory Compaction Characteristics Using Servopac Gyratory Compator", *Transportation Research Record*, No. 1630, pp. 89-97 (1998).

DeSombre, Rachel., Newcomb, David E., Chadbourn, Bruce and Voller, Vaughn, "Parameters to Define the Laboratory Compaction Temperature Range of Hot-Mix Asphalt", *Journal of the Association of Asphalt Paving Technologists*, vol. 67, pp. 125-152 (1998).

Mallick, Rajib B., "Use of Superpave Gyratory Compactor to Characterize Hot Mix Asphalt (HMA)", *Transportation Research Board $78^{th}$ Annual Meeting*, Jan. 10-14, 1999.

* cited by examiner

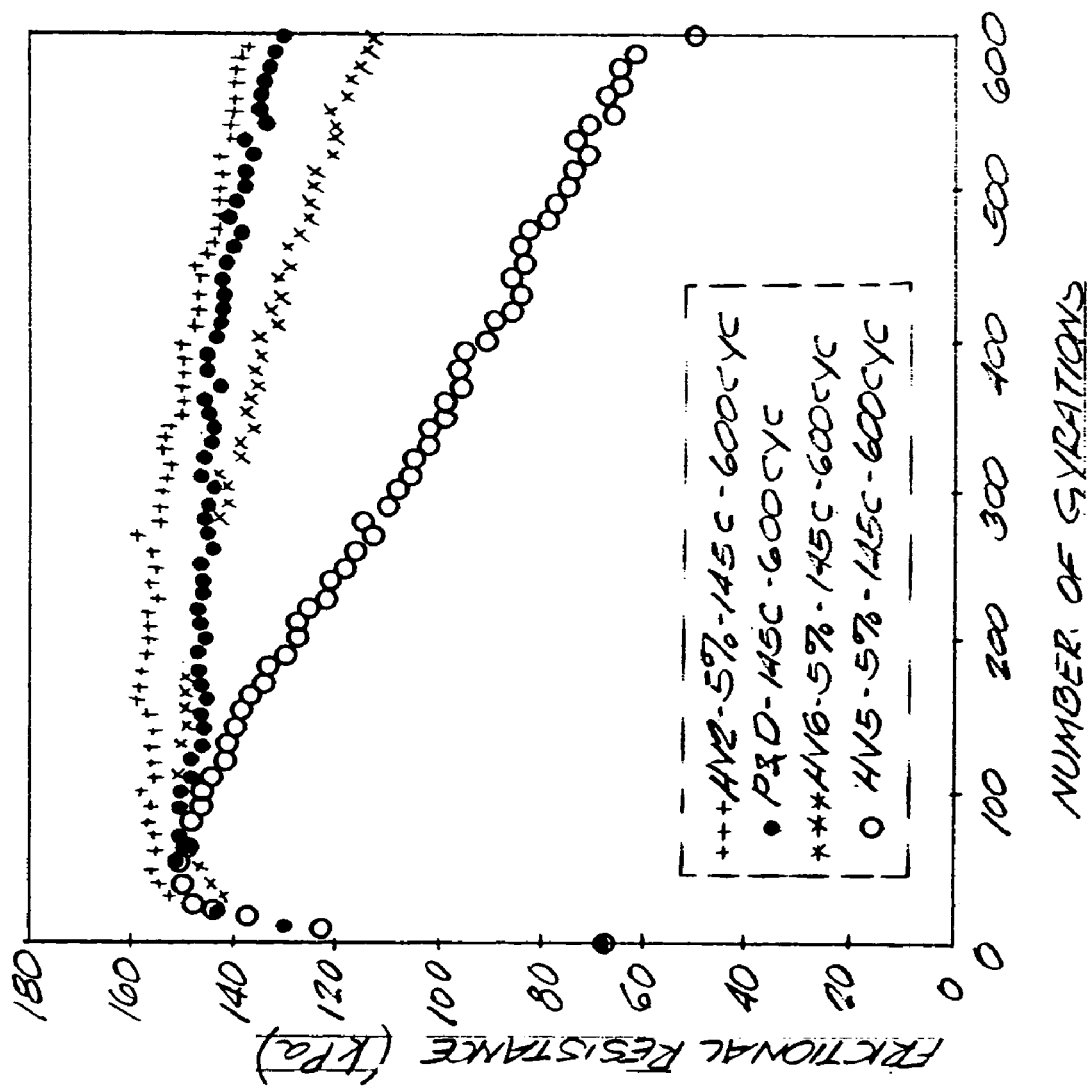

APPARATUS AND METHOD FOR TESTING MATERIAL PERFORMANCE

CROSS-REFERENCE TO RELATED APPLICATIONS

This patent application is a continuation of prior U.S. patent application Ser. No. 09/803,416, filed Mar. 9, 2001, now U.S. Pat. No. 6,694,823, which claims priority benefit of U.S. Provisional Patent Application No. 60/191,535, filed Mar. 23, 2000.

STATEMENT REGARDING FEDERALLY SPONSORED RESEARCH OR DEVELOPMENT

This invention was made with United States government support awarded by the following agencies:

TRANS DTFH71-97-TE039-WI30

The United States has certain rights in this invention.

FIELD OF THE INVENTION

The present invention relates generally to an apparatus and method for testing material performance and in particular to an apparatus and method for testing paving material performance. More particularly, the present invention relates to a gyratory compactor used for analyzing paving material performance. Specifically, the present invention relates to a gyratory compactor which includes an apparatus and method which measures a particular performance variable, such as shear resistance, of paving material specimens in order to predict the stability or suitability of the associated paving materials for actual use in vehicular supporting surfaces such as roads, parking lots, runways, and the like.

BACKGROUND OF THE INVENTION

Currently, in the United States alone, approximately 500 million tons of asphalt paving material mixtures are produced in any given year. Generally, only about 100 tons of asphalt mixtures are tested for quality purposes. As a result, laboratory testing of these mixtures greatly contributes to the design of high performance asphalt pavements.

There are many known different paving material testing machines and methods. Examples of such machines and/or methods are disclosed in the following patents, the teachings of which are hereby incorporated in their entirety by reference:

| U.S. PAT. NO. | INVENTOR |
|---|---|
| 2,972,249 | McRae et al. |
| 3,478,572 | McRae et al. |
| 4,502,338 | Smith et al. |
| 5,036,709 | McRae |
| 5,275,056 | Hamilton et al. |
| 5,456,118 | Hines et al. |
| 5,606,133 | Hines et al. |
| 5,817,946 | Brovold |
| 5,911,164 | McRae |
| 5,916,504 | Edwards, Jr. et al. |
| 5,939,642 | King et al. |

A common objective of known material testing machines is to subject test specimens to conditions which simulate actual use. For paving material test specimens, this requires simulation of the kneading forces applied to the paving materials by the tires of the vehicles passing thereover. It is generally understood in the art that simply applying a compressive force to a test specimen does not adequately simulate the kneading action of vehicular traffic. As a result, compaction machines that gyrate a test specimen during compression have been developed to better simulate actual conditions of use.

An example of such a gyratory compactor is the Gyratory Testing Machine (GTM) developed by the United States Corps of Engineers. Other examples of gyratory compactors are shown and described in some of the U.S. patents identified above. It is generally understood that gyratory compactors are effective tools in evaluating paving materials such as hot mix asphalt (HMA). Gyratory compactors generally have the flexibility of being adjusted to simulate various environmental conditions as well as the tire pressures of any traffic type including cars, trucks and aircraft. An important aspect of gyratory compactors is their ability to monitor the change in mixture response with densification under simulated field conditions. It has been shown that gyratory compactors are capable of achieving the ultimate density of paving materials that is actually obtained in the field. It has also been shown that gyratory compactors can be used for mixture design or quality control of paving materials.

Various governmental bodies have established standards for preparing and testing material specimens so that the properties of the test specimens approximate those of the actual material during construction, under use and over time. For example, the American Association of State Highway and Transportation Officials (AASHTO) has developed a standard (TP4-93) for preparing and determining the density of HMA test specimens by means of gyratory compactors having certain specifications. These gyratory compactors are classified as Superpave™ Gyratory Compactors (SGC). This particular AASHTO standard is used to prepare test specimens which simulate the density, aggregate orientation and structural characteristics obtained in the actual vehicular supporting surface when proper construction procedure is used in the placement of the paving material. Moreover, the AASHTO has developed other standards such as standard (MP2-95) which specifies the minimum quality requirements for asphalt binder, aggregate, and HMA for Superpave™ volumetric mix designs.

Current testing procedures use gyratory compactors to test mixture performance based on the number of applied gyrations and measured volumetric properties of the compacted test specimens. The volumetric design procedure measures the percentage of air voids in a test specimen as a function of the amount of compaction applied. It has recently been observed that the use of gyratory compactors for the evaluation of test specimens based on current specifications, particularly volumetric specifications, does not accurately predict expected field performance for paving materials. A vexatious problem, largely unattended in the art, concerns the lack of an apparatus and method to reliably and economically measure mechanical properties of test specimens subjected to a gyratory compaction process to more accurately predict the expected life cycle of any particular pavement mixture. A significant criticism of the current testing procedures utilizing gyratory compactors, particularly the Superpave™ volumetric design procedure, is the lack of a direct measure of mechanical properties of test specimens and the reliance on the control of densification characteristics of test specimens to predict field performance of paving materials. What is needed is an apparatus and method which is capable of measuring mechanical properties of paving material test specimens. What is further needed is an apparatus and method which predicts paving material performance based on the shear resistance of test specimens subjected to a gyratory compaction process.

Some prior art gyratory compactors have attempted to respond to the problem of lacking a direct measure of mechanical properties of paving material test specimens. It is known that certain gyratory compactors measure the force required for maintaining the angle of gyration. Generally, such known gyratory compactors measure the moment applied to a test specimen mold to maintain the gyration angle. Others have hypothesized that the densification curve used in the current volumetric design procedure can be used to estimate the resistance of test specimens to densification using the approximate energy indices as an alternative to a direct measure of shear resistance.

Even so, one problem with the gyratory compactors which measure the force required to maintain the angle of gyration is that the measured force will include the compounding effects of the mechanical components of the gyratory machine. Such effects include, for instance, the mechanical losses of the mold tilting mechanisms of the gyratory compactors. Another problem with these types of gyratory compactors is that they only measure a uni-directional force applied to the test specimens. Thus, these types of gyratory compactors do not provide an accurate analysis of the mechanical performance of test specimens. Yet another problem with these types of gyratory compactors is that they are machine specific and depend on the particular mold and compactor design. Therefore, what might work for one gyratory compactor may not work for another.

Materials such as paving material test specimens subjected to a gyratory compaction process, can absorb mechanical energy in at least two different ways. The first concerns volume change (densification) and the second concerns shape change or resistance to shape change (distortion). A problem with using the densification curve under the volumetric design procedure to estimate the resistance to densification as an alternative to a direct measure of shear resistance is that it is not completely known if densification specifically correlates with distortion. Thus, the determined results may not accurately predict the expected performance of the paving materials.

Notwithstanding the known deficiencies associated with gyratory compaction equipment and processes, the art has not adequately responded to date with the introduction of a gyratory compaction device and process which is capable of directly measuring the resistance of pavement material test specimens to shearing. In addition, despite the recognition of the lack of a direct measure of mechanical properties by current gyratory compactor designs, the art has produced very little in the way of practical techniques for evaluating paving material test specimen performance in terms of internal shear resistance in order to more accurately predict the likelihood of actual paving materials to maintain their serviceability as well as integrity under vehicular loading in the field.

BRIEF SUMMARY OF THE INVENTION

According to one aspect of the present invention, there is provided an apparatus and method for determining the shear resistance of a paving material test specimen subjected to gyratory loading so as to better predict the compactability, serviceability, and potential resistance to wear or rutting of a related paving material designed for actual use in the field. More particularly, the apparatus and method of the present invention provides a measure, preferably continuous, of the resistance of a paving material test specimen to distortion under gyratory loading, preferably at a fixed angle. In sum, the apparatus and method of the present invention directly measures the resistance of a paving material test specimen to distort when subjected to a gyratory compaction process. The determined frictional resistance can be used to predict the expected potential of the related paving material for use in the field.

The foregoing is realized in one aspect thereof in which there is provided a gyratory compactor having a load-cell-plate-assembly (LCPA) which measures the resistance of a material test specimen to distort under gyratory compaction. The LCPA includes a load cell assembly which is sandwiched between two plates. Preferably, the load cell assembly includes at least three load cells which are substantially evenly spaced apart. The LCPA is positioned between the test specimen and a ram of the gyratory compactor. The load cell assembly measures the variation in the distribution of the forces applied to the test specimen by the ram during the gyratory compaction process.

According to one aspect of the present invention, the forces directly measured by the load cell assembly are used to determine the eccentricity or location of the resultant force applied to the test specimen by the ram during the gyratory compaction process. Preferably, the load cell assembly is electrically connected to a data acquisition system which is electrically connected to a computer system so that the forces measured by the load cell assembly are recorded in real time, thereby allowing the changes in the shear resistance of the test specimen relative to the number of gyrations to be continuously monitored.

According to one aspect of the present invention, changes in the magnitudes of the measured loads or forces on the load cell assembly and the resulting calculated eccentricity values for the resultant force can be used to evaluate performance variables of the test specimen, such as the internal frictional resistance of the specimen to distort. A principal feature of the present invention is the recognition that shear resistance is directly related to the eccentricity of the resultant force applied during the gyratory compaction process.

Therefore, a feature of the present invention is to provide an apparatus and method which directly measures the shear resistance of a paving material test specimen subjected to a gyratory compaction process.

Another feature of the present invention is to provide an apparatus and method which measures the eccentricity of the resultant load in real time as applied by a ram of a gyratory compactor during the gyratory compaction process.

Yet another feature of the present invention is to provide an apparatus and method which provides a two-dimensional measurement of the eccentricity of the resultant load independent of the tilting of a gyratory compactor.

Still another feature of the present invention is to provide an apparatus and method in which forces applied to a test specimen itself are measured directly, thereby eliminating losses which would exist due to the mechanical components of the mold tilting mechanism of a gyratory compactor.

A further feature of the present invention is to provide an apparatus and method which accomplishes the features set forth herein and which is capable of use in existing gyratory compactors without requiring significant changes to the designs of such compactors, and without requiring significant changes to the compaction and gyration processes employed by such devices.

Yet a further feature of the present invention is to provide an apparatus and method which directly measures the frictional resistance of a paving material test specimen in the same gyratory compactor that is used for determining the densification properties of the test specimen.

Still a further feature of the present invention is to provide an apparatus and method which eliminates the need for using a separate device apart from a gyratory compactor to directly measure the shear resistance of a test specimen.

Another feature of the present invention is to provide an apparatus and method which continuously measures shear resistance of a test specimen during a gyratory compacting process.

Another feature of the present invention is to provide an apparatus and method which measures paving material shear resistance under laboratory conditions in order to validate the quality of such material prior to field paving operations.

Another feature of the present invention is to provide an apparatus and method which evaluates mechanical characteristics as well as volumetric characteristics of a test specimen to more accurately predict material performance during construction, under load and is use.

Other features and advantages of the invention will become apparent to those skilled in the art upon review of the following detailed description, claims and drawings in which like numerals are used to designate like features.

BRIEF DESCRIPTION OF THE DRAWINGS

FIG. 8a is a plot showing maximum and minimum load cell amplitudes as a function of number of gyrations for the fine mixture test specimen of FIG. 6a.

FIG. 11 is a plot illustrating the effect of gradation on frictional resistance of different test specimens.

FIG. 12a is a plot illustrating the effect of asphalt content of a fine mixture test specimen having varying asphalt contents.

FIG. 12b is a plot illustrating the effect of asphalt content of a coarse mixture test specimen having varying asphalt contents.

Figure 1:
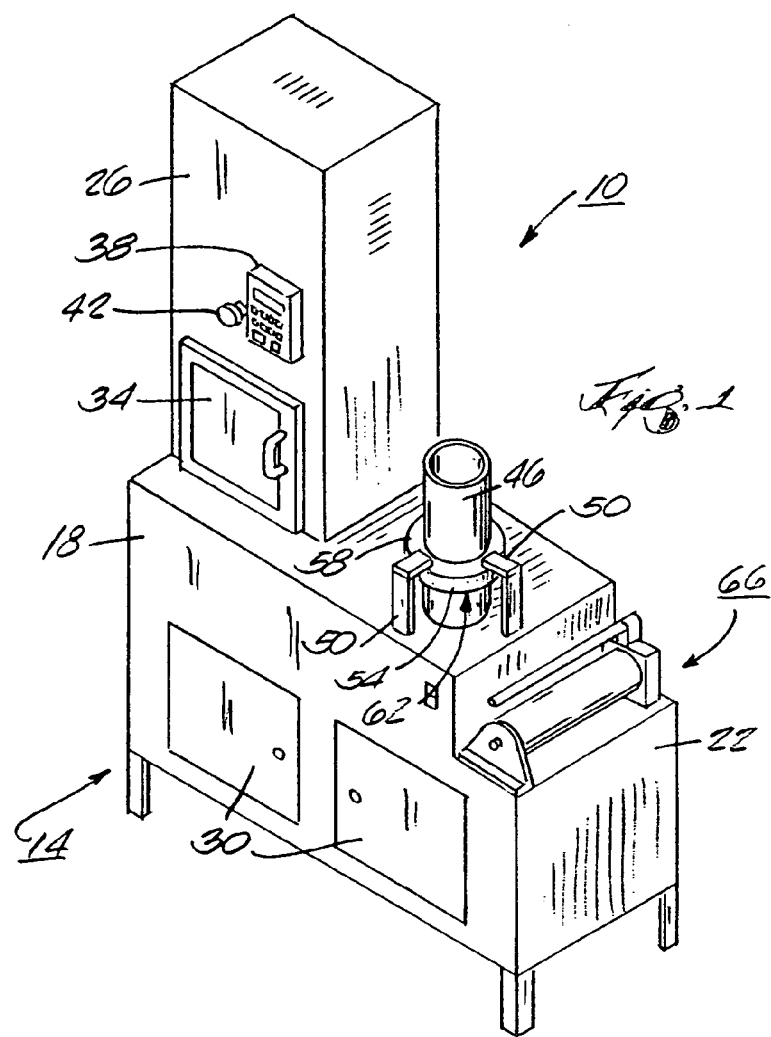
FIG. 1 illustrates a gyratory compactor in which the present invention is employed.

Before the embodiments of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein are for the purpose of description and should not be regarded as limiting.

DETAILED DESCRIPTION OF THE INVENTION

Illustrated in FIG. 1 is a gyratory compactor 10 in which the present invention is employed. It should be understood that the present invention is capable of use in other devices and in other gyratory compactors known in the art, and the gyratory compactor 10 is merely shown and described as an example of one such apparatus. One known gyratory compactor is available from the Pine Instrument Company of Grove City, Pa. under model or serial number AFGC125X.

The gyratory compactor 10 includes a frame 14 which supports a cabinet 18. The cabinet 18 includes a lower cabinet portion 22 and an upper cabinet portion 26. The lower cabinet portion 22 includes storage area access doors 30. The upper cabinet portion 26 includes an access door 34 to a mold and test specimen receiving chamber of the gyratory compactor 10. A control panel 38 for controlling the operations of the gyratory compactor 10 and an emergency stop button 42 are mounted upon the exterior of the upper cabinet portion 26. A cylindrical mold 46 for receiving a test specimen is held in a non-operational position on the top of the lower cabinet portion 22 by arms 50. The mold 46 includes an outwardly extending annular flange 54 having a top surface 58 and a bottom surface 62. An extruder, indicated generally at 66, for extruding a compacted test specimen from the mold 46 is mounted to the lower cabinet portion 22.

Gyratory compactors, such as the gyratory compactor 10 shown in FIG. 1, generally operate as follows. A specified quantity of paving material, such as an asphalt mixture, is placed within the mold. The mold is placed into an oven for pre-compacting heating to a specified temperature. The mold is removed from the oven and placed into the mold and test specimen receiving chamber of the gyratory compactor. Typically, a computer control system of the gyratory compactor is preprogrammed with certain testing parameters including constant compaction ram pressure, a particular angle of gyration, number and rate of gyrations and a final test specimen height as measured within the mold according to a predetermined percentage of air voids. At the push of a button, the computer initiates the test routine. The ram is placed into contact with a plate positioned on top of the test specimen in the mold. The carriage which holds the mold in the receiving chamber is tilted to obtain the desired gyration angle. The gyration and compaction process is commenced and continues at specified rates. At the completion of the test, the mold carriage is actuated to return the mold to a zero degree gyration angle to square the test specimen within the mold. The ram is retracted to a home position to allow removal of the mold from the gyratory compactor. The mold is placed in the extruder which is designed to push the test specimen out of the mold. Known gyratory compactors generally measure the densification characteristics of the test specimens. The volumetric design procedure measures the percentage of air voids in the test specimen as a function of the total number of gyrations and the amount of applied compaction load.

The overall construction and operation of gyratory compactors, such as gyratory compactor 10 shown in FIG. 1, has not been shown and described in great detail because the construction and operation thereof is not particularly significant in terms of the present invention. As noted and as will be further explained below, the present invention is capable of use in many gyratory compactors of varying designs having a number of different parameters.

Figure 2:
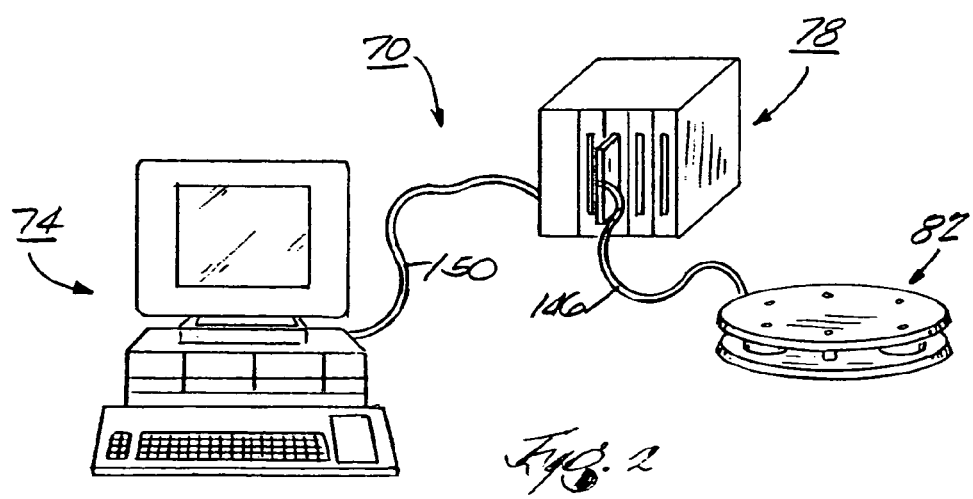
FIG. 2 is a schematic illustration of various components according to one aspect of the present invention showing the LCPA, a data acquisition system and a computer.

Illustrated in FIG. 2 is a schematic representation of a preferred assembly of the paving material performance testing device according to the present invention. The components of the overall assembly 70 include a computer 74, a data acquisition system 78 and an LCPA 82. The data acquisition system 78 may be a noise isolated data acquisition SCXI 1000 Box sold by National Instruments Corporation of Austin, Tex. Preferably, the data acquisition system 78 is controlled by a user friendly interface graphical program such as the software program LabVIEW™ sold by National Instruments Corporation of Austin, Tex. The overall function of the computer 74 and data acquisition system 78 will be more fully explained below. It should be noted that the LCPA is capable of use with any number of different data acquisition and/or computer systems. Moreover, other software known to those skilled in the art can be used instead of LabVIEW™. All that is required is that the data acquisition system, computer and software, utilizing appropriate algorithms, function to calculate various parameters based on the readings taken from the LCPA (described in detail below) and interpret the readings so that paving materials may be designed from the analysis of the performance parameters of the test specimens.

Figure 3A:
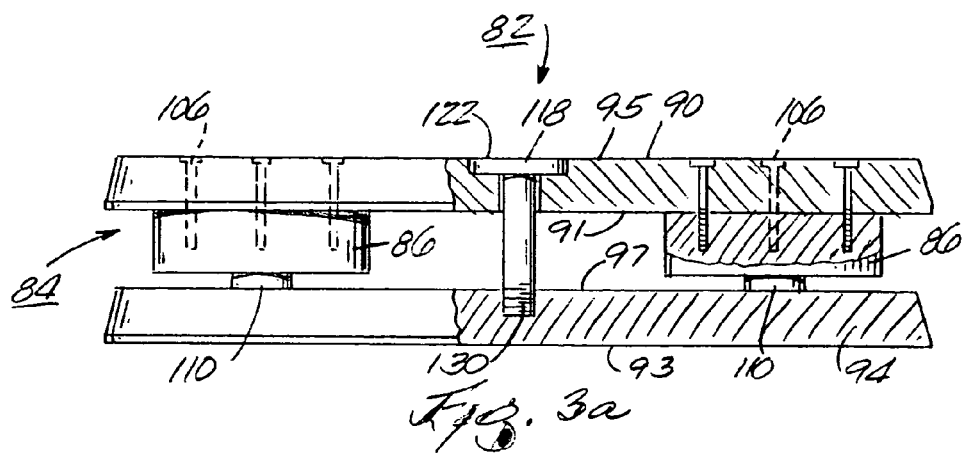
FIG. 3a is a partial cross-sectional view taken along line III—III of FIG. 3b of the LCPA as schematically shown in FIG. 2.
Figure 3B:
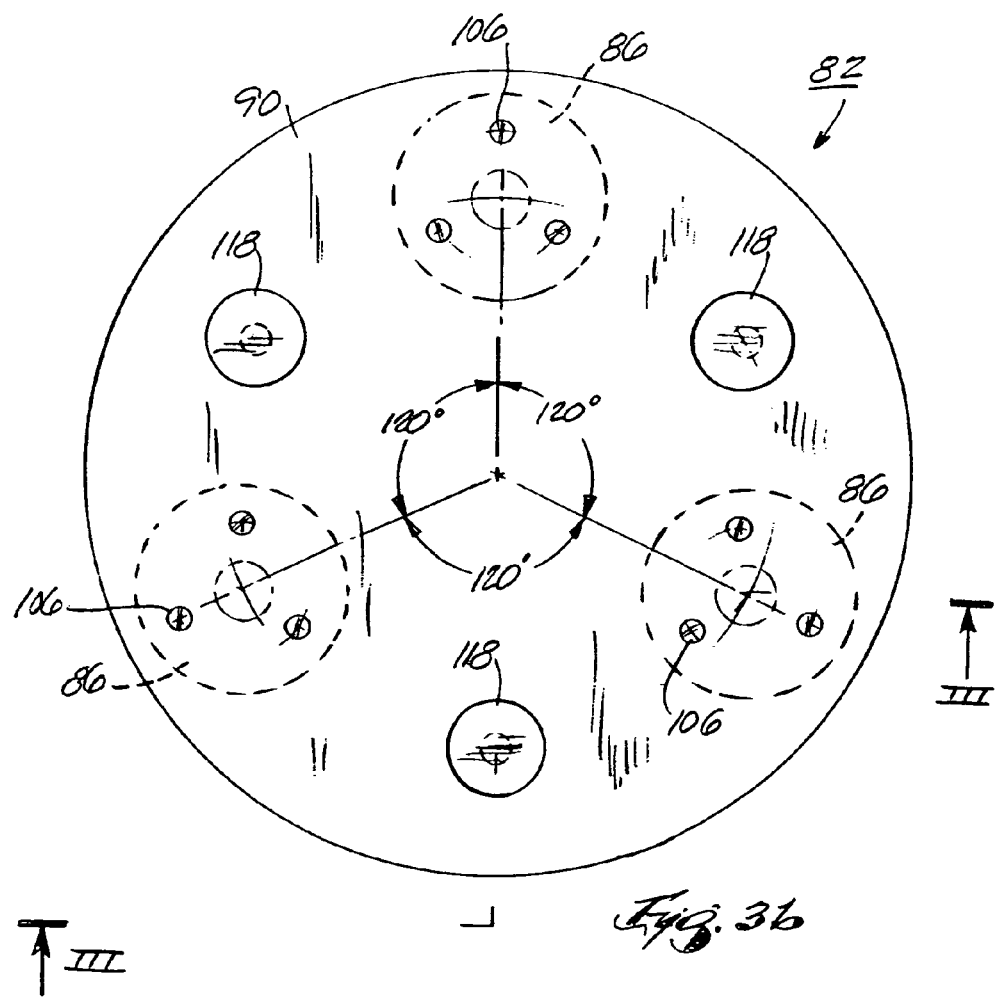
FIG. 3b is a top view of the LCPA as schematically shown in FIG. 2.

FIGS. 3a and 3b depict the components of the LCPA 82 of FIG. 2. The LCPA is a low-cost device which measures a spatial distribution of the shear resistance of a test specimen and which operates independently of the gyratory compactor design. One advantage of the LCPA is that it is versatile enough so that it can be sold as a component of a new gyratory compactor or retrofitted to operate within existing gyratory compactors. Specifically, the LCPA measures the variation in the distribution of the forces applied by the ram of the gyratory compactor on the test specimen during the gyration and compaction process. The variations in the distribution of the forces applied to the test specimen are used to calculate the location of the resultant force which is used to determine the frictional resistance of the test specimen. As will be further explained, shear or frictional resistance is an indicator of the potential resistance of a paving material to fail under field conditions.

The load cell assembly 84 preferably includes three load cells 86 positioned between an outer plate 90 and an inner plate 94. There are many known load cells capable of use according to the principles of the present invention. However, compression only load cells sold by Sensotec of Columbus, Ohio as Model 53 having a 2000 pound load carrying capacity, are suitable for use according to the present invention. The load cells are also preferably pre-calibrated for high temperature applications. Although more or fewer than three load cells may be utilized, at least three load cells are preferred in order to provide the desired spatial analysis of the forces applied to the test specimen. The plates 90 and 94 are preferably hardened steel plates which are capable of continued and repeated use for an acceptable period of time under the appropriate conditions. Each plate 90 and 94 includes an inner surface 91 and 93 and an outer surface 95 and 97, respectively.

To obtain the desired spatial analysis, the load cells 86 are preferably equally spaced 120 degrees apart and radially outward with respect to plate 90. The load cells 86 are each preferably provided with three tapped holes in the upper portion thereof for mounting to the outer plate 90 with fasteners such as screws 106. In this way, the load pin 110 of each load cell 86 has a small contact point on the outer surface 97 of the inner plate 94 when the LCPA is completely assembled. Alternatively, the load cells 86 can be connected to the outer plate 90 in any number of different ways so long as the load cells measure the distribution of the forces applied to the test specimen according to the principles of the present invention. The outer 90 and inner 94 plates are preferably held together and appropriately aligned by three connecting pins 118. Each head 122 of each connecting pin 118 is positioned flush with the outer surface 95 of the outer plate 90 and each threaded portion 130 of each connecting pin 118 threads into the inner plate 94. Alternatively, the outer 90 and inner 94 plates can be assembled together in any number of different ways according to the principles of the present invention, so long as the plates are properly aligned with respect to one another. Although not clearly shown, the diameter of the outer plate 90 is slightly smaller than the diameter of the inner plate 94 to minimize friction between the mold and the plates when the mold is tilted during the gyration and compaction process.

Figure 4:
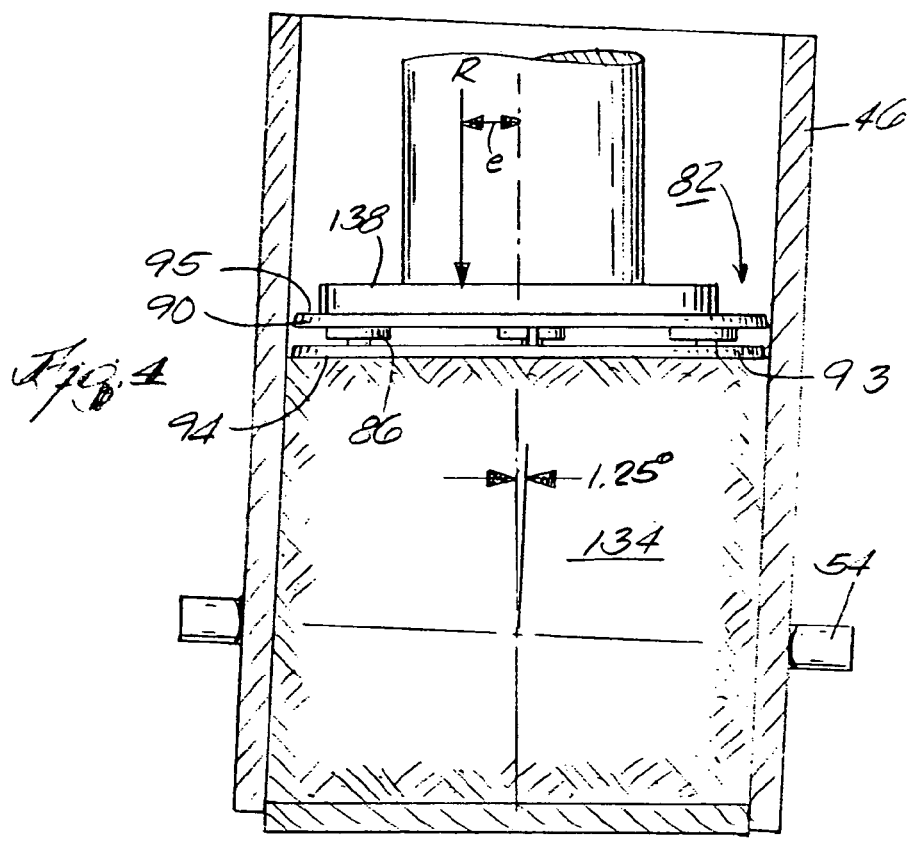
FIG. 4 is a schematic illustration of the LCPA of FIG. 2 placed into a mold of a gyratory compactor between a ram and a test specimen.

FIG. 4 is a schematic representation showing the LCPA 82 placed within a mold 46. Shown are the mold 46, the flange 54, the test specimen 134, the LCPA 82 and the ram 138 of the gyratory compactor 10. FIG. 4 also schematically illustrates the tilting of the mold during the gyration and compaction process. Although the tilt angle is shown as 1.25 degrees, the angle may vary depending on the type of gyratory compactor used. The LCPA 82 is placed on top of the test specimen 134 within the mold 46. Alternatively, the LCPA 82 could be located in other positions relative to the test specimen, depending on the design of the gyratory compactor. During the gyration and compaction process, the ram 138 contacts the outer surface 95 of the outer plate 90, and the inner surface 93 of the inner plate 94 contacts the top of the test specimen 134. The mold 46 is caused to tilt the appropriate amount, e.g., 1.25 degrees, and the ram 138 compacts the test specimen 134 according to known procedures. The mold gyrating equipment (not shown) gyrates the mold 46 through contact with the flange 54 as the ram 138 compacts the specimen 134. As will be further explained below, the location or eccentricity e of the resultant force R exerted by the ram 138 at any instant of compaction can be determined according to the principles of the present invention. Although the ram 138 typically exerts a constant force, the location of the resultant force R distributed on the specimen 134 changes because the distortion resistance of the specimen 134 changes over time as the number of gyrations increases. A reduction in frictional resistance means the shape of the specimen is more easily changed.

In conjunction with FIG. 2, the load cell assembly 84 is electrically connected to the data acquisition system 78 by a cable or wire 146, and the data acquisition system 78 is electrically connected to the computer 74 by a cable or wire 150. During the gyration and compaction process, the data acquisition system 78 and computer 74 record and interpret load measurement readings from the load cell assembly 84 for each gyration. It has been determined that 50 readings for each load cell 86 for each gyration provide a sufficient number of readings for an accurate analysis. However, more readings or fewer readings may be taken depending on the circumstances of the situation. Deflection readings or volumetric readings for the test specimen 134 are also recorded in real time through the serial communication port of the gyratory compactor 10 as is currently known. Having described the structural components of the apparatus for testing paving material performance according to the present invention, the method will now be more fully described.

Figure 5:
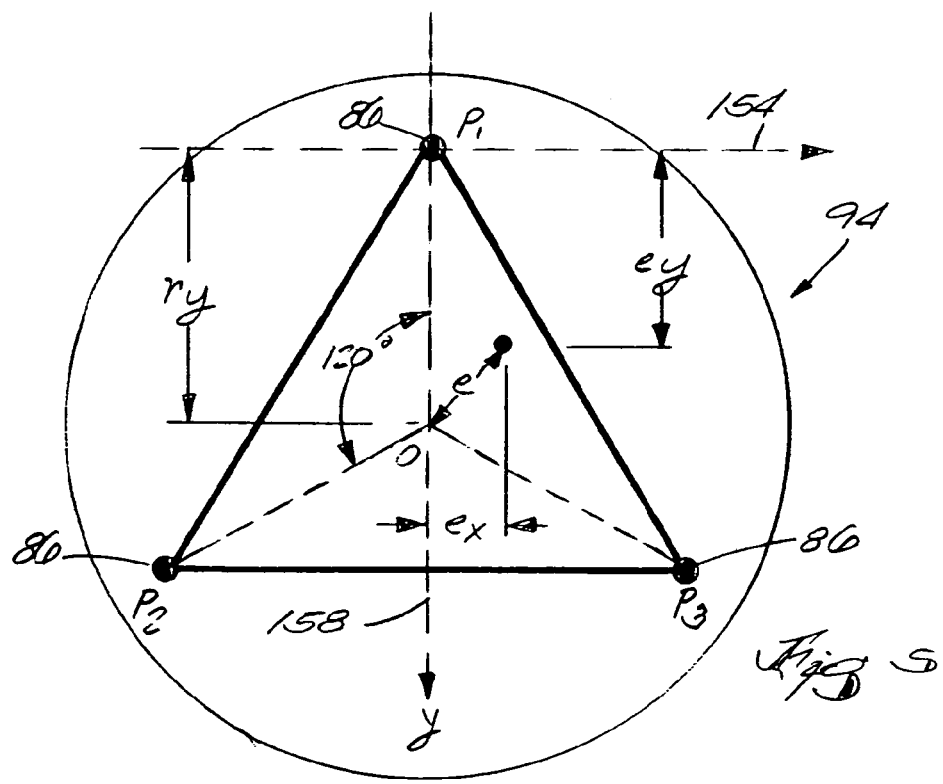
FIG. 5 schematically illustrates the geometrical relationships between the load cells of the LCPA of FIG. 2 so that the location of the resultant force applied by the ram on the test specimen as schematically shown in FIG. 4 can be determined.

The load cell assembly 84 measures in real time the distribution of the forces applied to the test specimen 134 during the compaction and gyration process. Based on these readings, two components of eccentricity ($e_x$ and $e_y$) of the total load relative to the center of the plate 94 can be calculated for each of the readings collected for each load cell 86 during each gyration. The calculations are computed using general moment equilibrium equations along two perpendicular axes 154 and 158 passing through the center of one of the load cells $P_1$ as shown in FIG. 5 and equation (A) below. The total resultant force R is calculated by the summation of the load cell forces ($P_1+P_2+P_3$) at any instance of the gyration. The $e_x$ and $e_y$ values represent the location of the resultant force R exerted by the gyratory ram 138 at an instance of compaction as shown schematically in FIG. 4.

$$\Sigma M_x = 0 \Rightarrow e_y$$

$$\Sigma M_y = 0 \Rightarrow e_x$$

$$e = \sqrt{e_x^2 + (r_y - e_y)^2} \quad (A)$$

where $P_1$, $P_2$ and $P_3$=load cell forces at equal distances to the coordinate axis, O; $e_x$, $e_y$=x and y components of eccentricity, e; $r_y$=location of the plate 94 center point with respect to the coordinate axis.

The eccentricity values can be plotted in a two-dimensional or three-dimensional plot to obtain a visual representation of the entire path of the resultant force R during the gyration cycles. As will be further explained below, the location of the resultant force as applied to a test specimen can be used as an indicator of how well a related paving material may perform in the field. The present invention is further explained by way of the following examples in cooperation with FIGS. 6–14 which are not to be construed as limiting the scope of the invention.

Figure 6A:
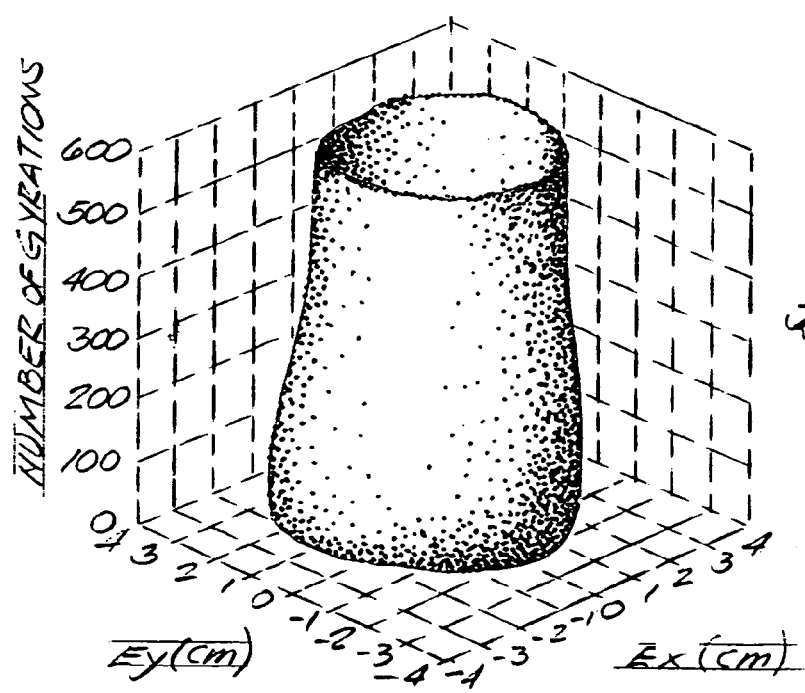
FIG. 6a is a three-dimensional eccentricity plot for a fine mixture test specimen.
Figure 6B:
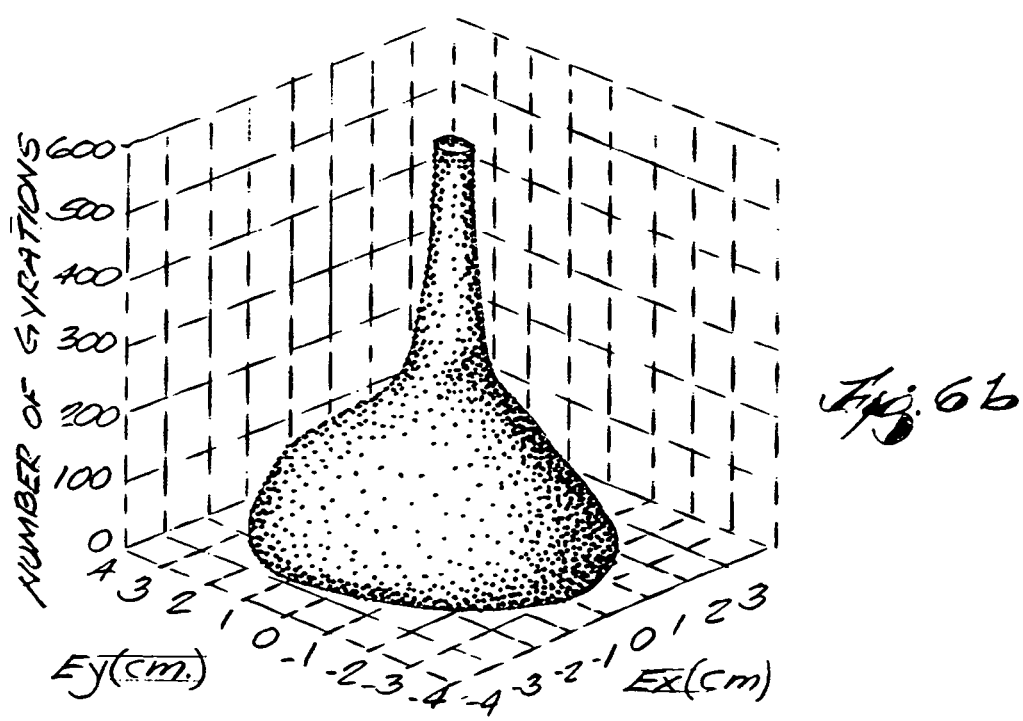
FIG. 6b is a three-dimensional eccentricity plot for a coarse mixture test specimen.

FIG. 6a illustrates a three-dimensional eccentricity plot obtained for one fine paving material mixture specimen with aggregate gradation above the maximum density line and above the restricted zone. The maximum density line and the restricted zone are common parameters found on aggregate gradation charts as known by those skilled in the art. FIG. 6b illustrates a three-dimensional eccentricity plot for one coarse paving material mixture specimen with aggregate gradation below the maximum density line and below the restricted zone. The details of aggregate gradations and mixture designs are known to those skilled in the art. For this example, the test specimens were compacted at 135° C. at an asphalt content of 6.5%. Both test specimens were compacted to 600 gyrations. As can be observed, there is a significant difference in the eccentricity plots of the tested specimens.

At the beginning of the gyrations, the measured eccentricity is low for each test specimen because of the excess air voids that effectively reduce the frictional resistance of the test specimens to densification. Both test specimens exhibit a similar trend at the initial gyrations. The eccentricity values progressively increase as the gyrations continue until a critical number is reached at which time both test specimens show maximum eccentricity values caused by their respective maximum frictional resistance. As more gyrations are applied, the test specimens significantly deviate in behavior. The fine mixture specimen shown in FIG. 6a continues to offer high eccentricity values, which are indicative of high frictional resistance to distortion. On the other hand, the coarse mixture specimen shown in FIG. 6b starts showing a progressive decrease in the eccentricity values, which are indicative of a reduction in the frictional resistance to distortion. The greater the frictional resistance of the test specimen to distortion, the greater the moment that is needed to compact the specimen. Accordingly, the greater the frictional resistance, the farther away the resultant force R will be from the center of the test specimen. If the test specimen is easily shaped during the gyration and compaction process, the moment needed to compact the specimen is smaller. Accordingly, the lower the frictional resistance, the closer the resultant force R will be to the center of the test specimen. The more the frictional resistance is reduced, the easier it is to change the shape of the specimen during the testing process. Therefore, according to the principles of the present invention, shear resistance is measured as a factor of gyrations which correlates to an indication of stability. The less frictional resistance exhibited by a test specimen, the more likely the related paving material will fail in the field as a result of wear or rutting. In terms of the results obtained in this example, it could be predicted that the coarse mixture shown in FIG. 6b is more likely to fail in the field than the fine mixture shown in FIG. 6a.

Figure 7B:
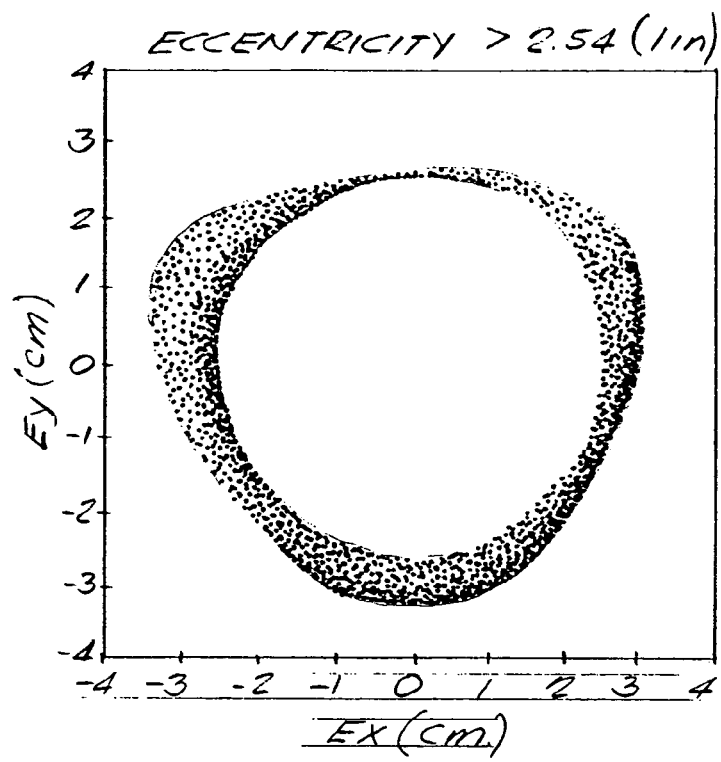
FIG. 7b is a two-dimensional eccentricity plot for the coarse mixture test specimen of FIG. 6b having eccentricity points greater than 2.54 cm.
Figure 7A:
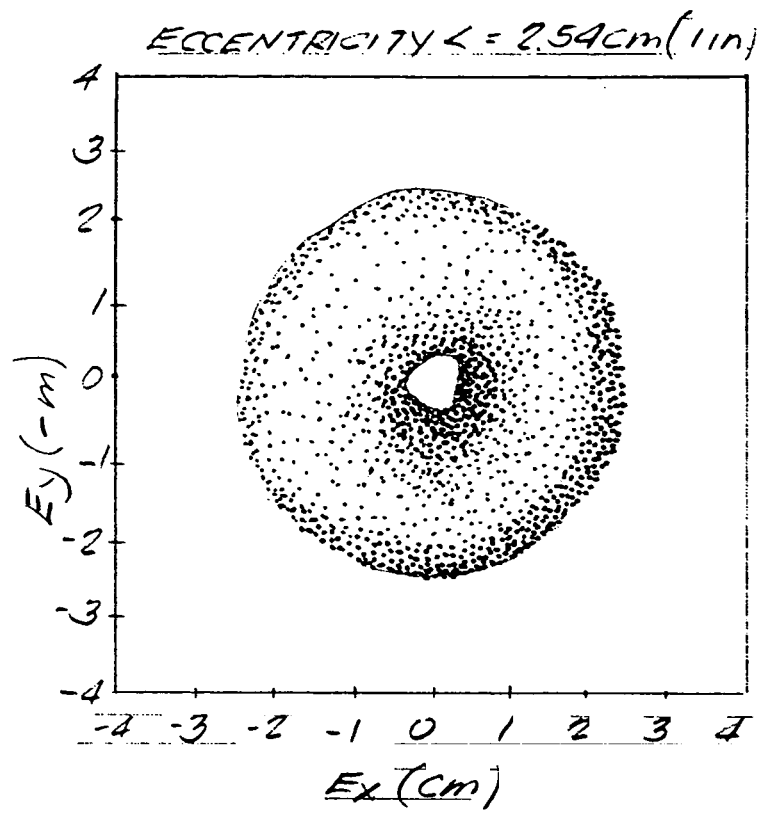
FIG. 7a is a two-dimensional eccentricity plot for the coarse mixture test specimen of FIG. 6b having eccentricity points smaller than 2.54 cm.

FIGS. 7a and 7b illustrate two-dimensional eccentricity plots for the coarse mixture of FIG. 6b. It should be noted that certain insignificant errors may be obtained when calculating the eccentricity values based on the readings from the load cells as described herein. It can be observed in FIG. 7a that the data points for eccentricity values smaller than 2.54 cm display a circular pattern, whereas the data points for eccentricity values greater than 2.54 cm display a triangular trend (FIG. 7b). It has been determined that the reason for these different trends is attributable to the positions of the load cells relative to the center of the plate. As the eccentricity of the resultant force R exceeds the position of a straight line connecting two adjacent load cells (see FIG. 5), the calculated value cannot reflect the actual eccentricity because the third load cell will be under tension force. Since the load cells are preferably not connected to the plates such that they can measure a tension force, this load cell is recording the value of zero, which leads to error in calculating the actual eccentricity value. The eccentricity value, however, is not in error when the resultant force R is along a radial line from the center of the plate passing through the center of any of the load cells. Although the use of additional load cells can mitigate this problem, it is believed that the three eccentricity values that can be obtained for each cycle as described herein, gives a good representation of the actual eccentricity distribution according to the principles of the present invention. Because the eccentricity values estimated in between the load cell locations could not give an accurate representation of the measured eccentricities, only the data points collected when the resultant force R was along the radial lines passing through the load cells were used in the calculation of the frictional resistance.

Figure 8A:
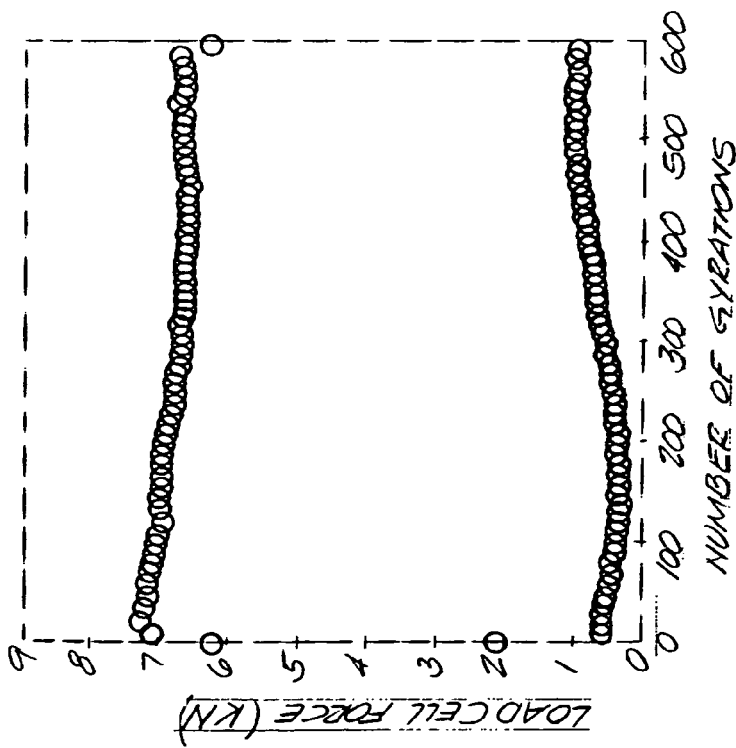
Figure 8B:
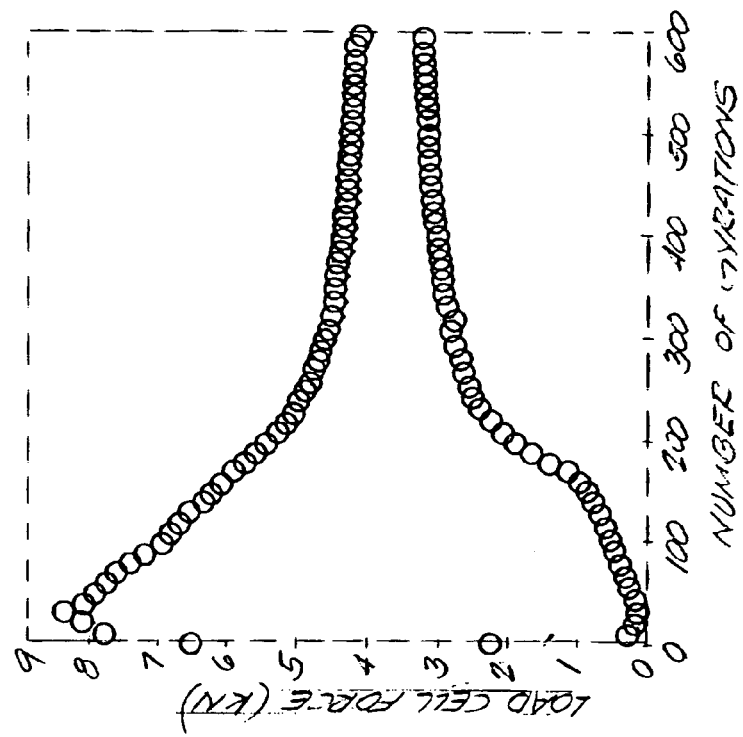
FIG. 8b is a plot showing maximum and minimum load cell amplitudes as a function of number of gyrations for the coarse mixture test specimen of FIG. 6b.

To better understand the difference in the behavior of the test specimens, the amplitude of the load carried by one of the load cells for each of the test specimens is shown in FIGS. 8a and 8b. The plots show the maximum and minimum load carried by the load cell during each of the 600 gyrations. The plots depict the same trend as in FIGS. 6a and 6b. It can be observed that the fine mixture specimen (FIG. 8a) maximum amplitude is 7 kN which is lower than the maximum amplitude of 8.5 kN reached by the coarse mixture specimen (FIG. 8b). It can be observed, however, that the fine mixture specimen maintains the load amplitude throughout the 600 gyrations with only a minor change. For the coarse mixture specimen, the load amplitude starts decreasing rapidly after it reached the maximum load at approximately 35 gyrations. The reduction in load amplitude reaches the minimum at about 400 gyrations after which the load amplitude resembles the resistance of a mixture with no shear resistance, as can be measured by using a rubber balloon filled with water.

The load amplitude plots in FIGS. 8a and 8b help explain the eccentricity variations shown in FIGS. 6a and 6b. It appears that depending on the aggregate gradation, mixtures can initially offer different resistance to distortion and densification. A mixture can maintain this level of frictional resistance to a high number of gyrations (FIG. 8a), or it can start losing the frictional resistance with increased number of gyrations (FIG. 8b). These trends are important because they could be related to observations in the field where rutting is observed for some mixtures after increased number of traffic load applications. These trends are also important because they can be related to other phenomenon reported for granular materials during which hardening is observed under repeated loading followed by softening due to preferred orientation of aggregates. In granular materials, it has been shown that stability of a mixture can be explained by the evolution of the internal structure of aggregates. A simple technique based on granular mechanics to quantitatively evaluate the aggregate structure in asphalt mixtures is known by those skilled in the art. This technique has shown that with increasing number of gyrations, the vector magnitude of the aggregate orientation initially increases, reaches a maximum and then decreases with increased number of gyrations. This trend is compatible with the trends observed for the coarse mixture in FIGS. 6b, 7a–b and 8b, and could be used to explain this type of behavior.

According to the present invention, it is believed that the calculated change in the magnitudes of the measured loads at each load cell and the resulting eccentricity values can be used to study the internal frictional resistance of the specimen to densification and distortion. Frictional shear resistance can be calculated using the energy concept by equating the strain energy of the test specimen to the energy of the external forces. Assuming that at any gyration the specimen is fully constraint, and the energy due to surface traction is negligible, the energy balance for the mixture specimen at any gyration cycle can be written using the following equation:

$$W=U \tag{B}$$

where W=work of external forces; and U=total strain energy of sample.

Figure 9:
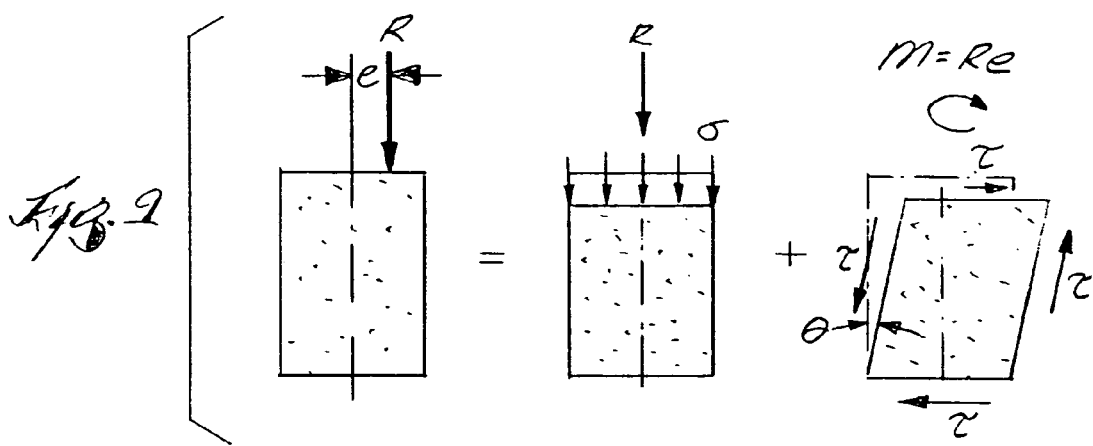
FIG. 9 schematically illustrates applied external forces and stress distributions to a test specimen in the determination of frictional shear resistance of the specimen according to the principles of the present invention.

As shown in FIG. 9, the moment M can be calculated by multiplying the resultant ram force R by the average eccentricity e measured by the LCPA for any given gyration cycle. The frictional shear resistance FR, represented by $\tau$, applied to the test specimen can be determined from equation (C):

$$\tfrac{1}{2}M\theta = \tfrac{1}{2}\tau\gamma V \tag{C}$$

where M=applied moment during gyration; $\theta$=tilt angle (radians); $\gamma$=shear strain; $\tau$=frictional resistance; and V=sample volume at any cycle.

Since the tilt angle $\theta$ is equal to the strain $\gamma$, equation (C) can be further simplified to calculate the frictional shear resistance FR as follows:

$$FR = \tau = \frac{Re}{Ah} \tag{D}$$

where A=sample cross-section area; and h=sample height at any gyration cycle.

In the conventional volumetric test procedure the asphalt content, the aggregate gradation, and the aggregate angularity are some of the important variables that are typically varied in a test specimen. These factors are also recognized to have a major impact on paving material performance in the field. To evaluate whether the LCPA can measure the effects of these variables and whether it can show trends similar to what is known in the field, a number of test specimens were prepared and tested at selected conditions. Asphalt content, aggregate gradation and percent natural sand were varied. The following provides an explanation of the observations from this study.

Figure 10:
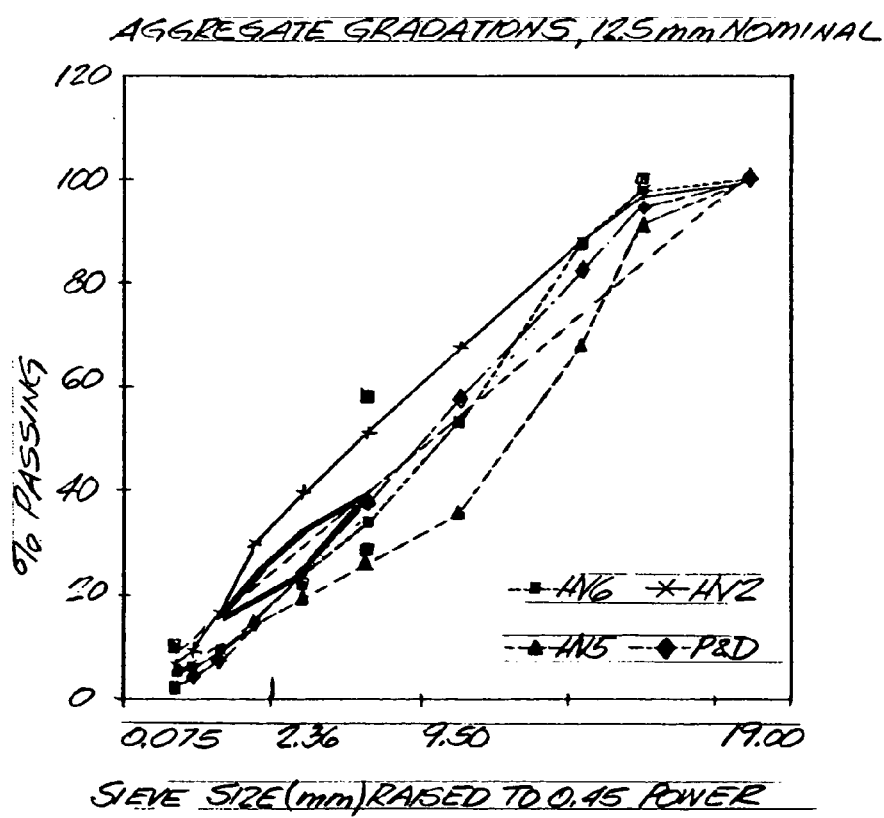
FIG. 10 is a gradation chart for various pavement samples.
Figure 22B:
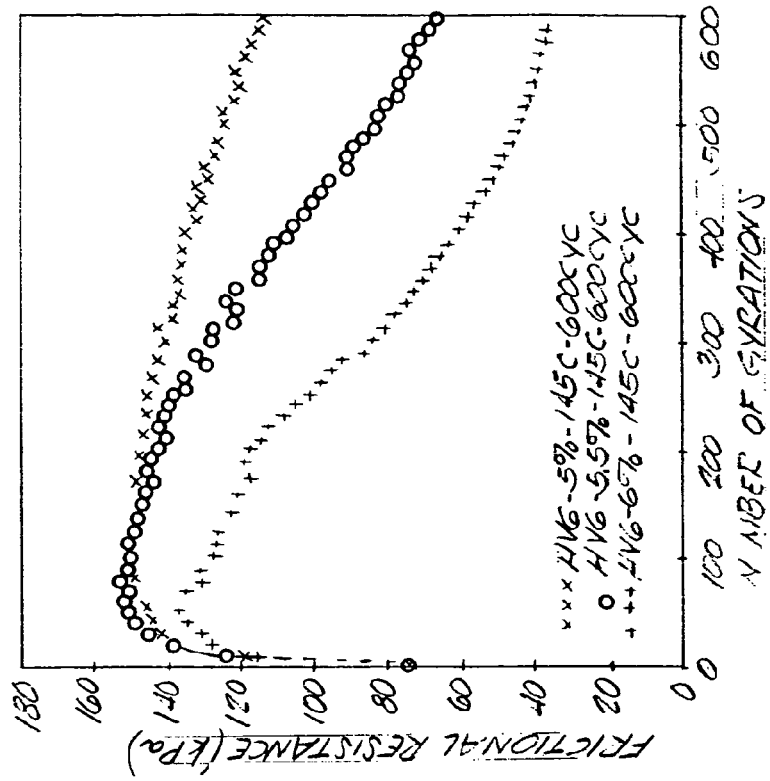
Figure 22A:
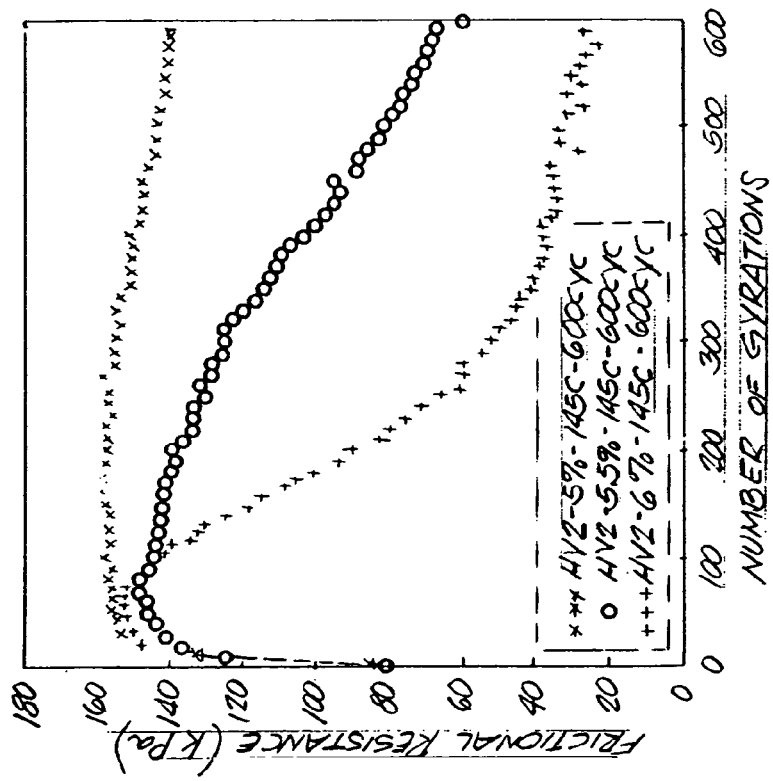

The gradations used for the study, as shown in FIG. 10, included a very fine gradation (HV2), a very coarse gradation (HV5), an "S" shaped gradation (HV6), and a typical mixture used in the field by Payne and Dolan Inc. (P&D). All gradations were made with crushed limestone from one source in Wisconsin with no natural sand included. P To study the effect of aggregate angularity, two other test specimens were prepared using the same fine gradation HV2 and the same coarse gradation HV5 but the manufactured sand was replaced with natural sand of low angularity (FAA=39).

To relate to actual mixtures produced in the field, the P&D gradation selected by the P&D laboratory was tested with and without the inclusion of reclaimed asphalt pavement. To represent the results, the data collected for each test specimen was used to calculate the values of the frictional resistance based on the average eccentricity values calculated for each cycle. The values of frictional resistance were plotted as a function of the number of gyrations as shown in FIG. 11. The beginning and the end of each cycle were chosen arbitrarily by the time the peak to peak load on each of the load cells was reached. The peak loads were then used to calculate the average FR value for a given test specimen sample. Frictional resistance values are preferred over eccentricity values because FR takes into account the change in volume, as shown in equation D above.

Effect of Aggregate Gradation

The effect of aggregate gradation on frictional resistance for the tested specimens, at a given asphalt content of 5% (by weight), is shown in FIG. 11. It can be observed that during the first 80 gyrations, the test specimens showed a similar increase in the FR values. After 100 gyrations, the test specimens started showing significant variations in frictional resistance and the rate of change increased with the number of gyrations. The HV5 mixture specimen shows the lowest resistance, which is a coarse mix with gradation falling under the maximum density line (see FIG. 10). On the other hand, the test specimens that maintained the highest resistance were the fine mix HV2 which is above the maximum density line, and the P&D test specimen which is designed for certain field applications.

This difference in behavior suggests that the LCPA of the present invention is effective in measuring effects of change in specific aggregate size distribution during the gyration and compaction process. The differences could be logically attributable to the variation in the interaction between aggregates of particles with varying size distribution. It is reasonable to suggest that the fine mixture behavior is due to the increased number of contact points within the mixture while the weakness of the coarse mixture is the lack of sufficient contact points within the mixture. It is also reasonable to suggest that the relative change on orientation of aggregates causes the observed differences.

Effect of Asphalt Content

The effect of asphalt content on the development of the frictional resistance and the change with gyrations for the HV2 and HV6 test specimens are compared in FIGS. 12a and 12b. It can be observed from the data that increasing the asphalt content from 5% to 6% has considerable impact on the frictional resistance of the HV2 test specimens. The effect is also significant on the HV6 test specimens but it appears to be more gradual particularly at the 6% asphalt content. It is interesting to note that most of the changes are observed at high number of gyrations, usually after 50 to 100 gyrations. It is also evident that the peak frictional resistance was reached earlier at around 50 cycles for 6% asphalt content while it took an additional 60 cycles to reach the peak resistance at lower asphalt content.

The reduction in resistance for HV2 and HV6 at higher asphalt content are expected because it is known that the excessive binder content causes a reduction in aggregate to aggregate contact. The more gradual change for the HV6 mixture relative to the HV2 mixture can be attributable to the effect of gradation in these mixtures. It may also be stated, based on these results, that using a better gradation may improve frictional resistance while the detrimental effect of excessive asphalt content may be prevented. One of the interesting points in the behavior of HV2 is that it appears to be very sensitive to asphalt content as evident by the dramatic change in the frictional resistance when the asphalt changed from 5% to 6%. The behavior measured for HV2 at 6% shows that after 400 cycles the mixture lost almost 90% of its peak frictional resistance, which resembles an unstable plastic mixture. Similar arguments can also be made for HV6 mixtures, however the highest resistance throughout the entire gyration cycles may be reached at an asphalt content lower than 5% as seen in FIG. 12b. The lower bound for the resistance of HV6 is expected at an asphalt content higher than 6%.

Effect of Aggregate Angularity

Effect on aggregate angularity was studied on the fine gradation HV2 and the coarse gradation HV5 by comparing the results before and after replacing the manufactured sand with natural sand. The fine gradation with natural sand MV2 was compared with HV2, and the coarse gradation with natural sand MV5 was compared with HV5. The relative proportions used in these mixtures are shown in Table 1.

TABLE 1

| Percentage of Manufacture and Natural Sand Included in Test Specimens | | | | |
|---|---|---|---|---|
| | HV2 | MV2 | HV5 | MV5 |
| Manufacture Sand (%) | 22 | 9 | 23 | 0 |
| Natural Sand (%) | 15 | 27 | 6 | 21 |

Figure 13A:
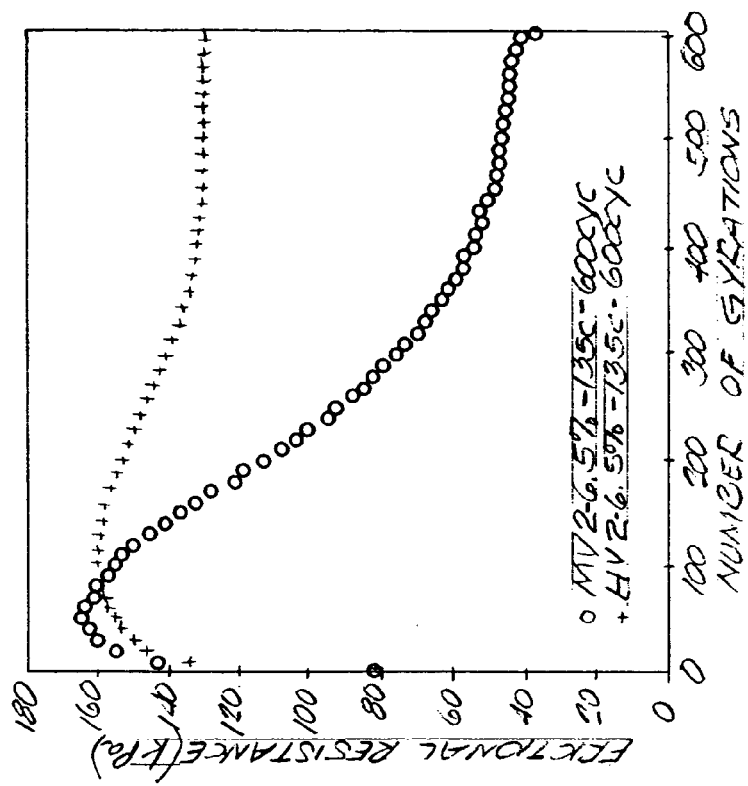
FIG. 13a is a plot illustrating the effect of aggregate angularity on fine and coarse mixture test specimens.
Figure 13B:
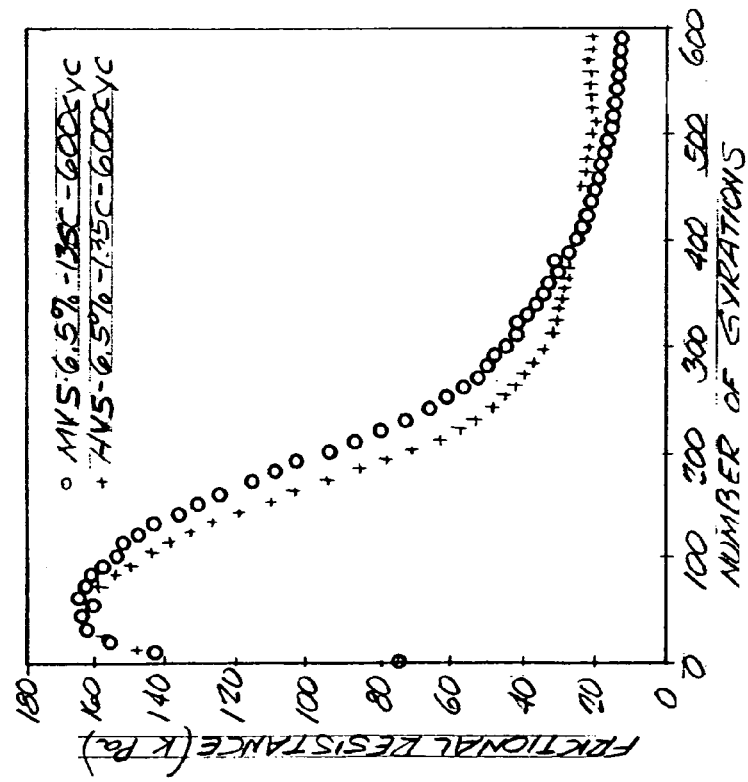
FIG. 13b is a plot illustrating the effect of aggregate angularity on fine and coarse mixture test specimens.

The effect of angularity for the tested mixtures on the frictional resistance is plotted in FIGS. 13a and 13b. There are minor differences in the gradation as well as volumetric properties (e.g., Superpave™ requirements) of the HV and the MV mixtures. As seen in FIG. 13a, a higher amount of natural sand caused a considerable decrease in frictional resistance for the fine gradation HV2 and MV2 mixtures. However, this effect is not seen in the coarse HV5 and MV5 mixtures at the same asphalt content and compaction temperature, as observed in FIG. 13b. It appears that because of the increased points of contacts in the finer gradations, the natural sand, due to its roundness, can cause significant reduction in frictional resistance. For the coarse gradation, this is not the case possibly because of the reduced number of contact points between the aggregates. The results collected indicate that the measurements with the LCPA of the present invention can be very sensitive to the inclusion of sand with low angularity. The results suggest that the interaction between gradation and aggregate angularity may play a role in the overall stability and serviceability of a paving mixture.

Relationship Between Air Voids and Frictional Resistance

It has been demonstrated that the LCPA of the present invention can be effectively used to measure the overall frictional resistance of asphalt mixtures. It has also been shown that the frictional resistance is sensitive to asphalt content, aggregate gradation, and aggregate angularity. A feature of the present invention is to supplement the volumetric design procedure traditionally used for analyzing test specimens with the frictional resistance calculations set forth herein. Currently, there exists charts which plot desired volumetric properties for test specimens. These same charts can be modified to include frictional resistance measurements as determined according to the present invention in order to provide a more complete analysis of the performance of a particular test specimen. For example, the same chart currently employed by the Superpave™ volumetric test, which includes the % Gmm as a function of number of gyrations, can be modified to include frictional resistance as another variable as a function of number of gyrations. This new plot can be called a volumetric-stability plot.

Figure 14:
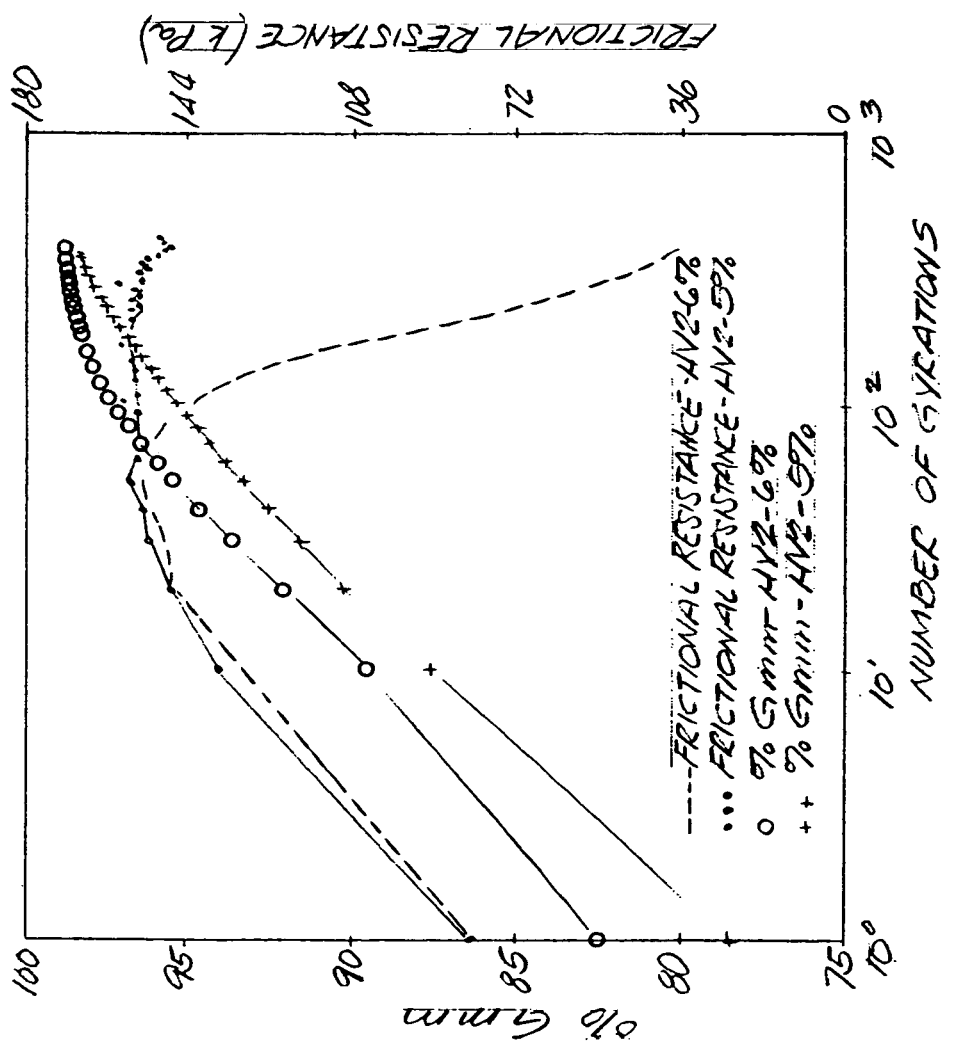
FIG. 14 is a plot illustrating the volumetric stability and frictional resistance of a fine mixture test specimen.

FIG. 14 is an example of such a volumetric-stability plot for an HV2 mixture having two different asphalt contents. Similar to the limits currently used for the volumetric properties at a selected number of gyrations, limits for the frictional resistance could be specified at the same or different number of gyrations. According to the present invention, it is suggested that frictional resistance is a good indicator of the stability of an asphalt mixture. As shown in FIG. 14, it does not appear that there is a strong relationship between the value of frictional resistance and volumetric properties. The two mixtures shown have both reached 98% Gmm at approximately the same number of gyrations. Thus, both mixtures passed the volumetric test and they both would have been expected to perform well in the field. However, the measured resistance for the 5% asphalt content is 4–5 times higher than the value for the 6% asphalt content. According to the present invention, even though both specimens passed the volumetric test, it is suggested that the 6% asphalt content mixture may result in significant rutting and distortion in the field while the 5% mixture, which maintained a high level of resistance, should perform better.

An interesting finding according to the present invention is that the frictional resistance reaches a peak at approximately 94%–96% Gmm. Some mixtures lose their resistance very rapidly when % Gmm exceeds these limits while others are capable of maintaining a high percentage of resistance for a large number of cycles and higher values of % Gmm. This information may be used to better predict the performance of a particular paving material.

Possible Method for Using % Gmm and Frictional Resistance for Mixture Design

The results collected in the studies indicate that the LCPA could be used to improve the mixture design procedure by providing a measure of the frictional resistance of test specimens to compaction. One plausible approach to incorporate the results from the LCPA is to limit the frictional resistance to a maximum value at the initial number of gyrations to ensure compactability of the test specimen. This criteria could address the issue of harsh mixtures and should eliminate the concerns regarding some of the new mixtures being designed under the Superpave™ requirements. The criterion can be based on the FR value at 92% Gmm or on the total energy calculated by dividing the area under the FR curve by the area under the % Gmm curve between 86% Gmm and 92% Gmm. This value should represent the energy required to compact the mixture specimen between 14% air voids and 8% air voids, which represent typical field compaction conditions.

For traffic considerations, a similar approach could be used. A minimum frictional resistance at a selected number of gyrations could be specified or a minimum accumulated area under the FR curve could be used. This accumulated area represents potential energy offered by the mixture specimen to resist distortion under traffic. It is important to note that the FR values are normalized to the volume and thus the densification effect on resistance is accounted for.

The LCPA according to the present invention is used to determine the relationship between gyrations in the gyratory compactor and the traffic volume in the field. It is desirable to define the range in gyrations that is representative of various traffic volumes. It is also desirable to determine the relationship between the compaction effort by field conditions and the effort applied by the gyratory compactor. If such relationships are established, it would be possible to use the gyratory compactor as an even more effective tool in the designing of mixtures for better construction and better resistance to traffic damage.

Figure 15:
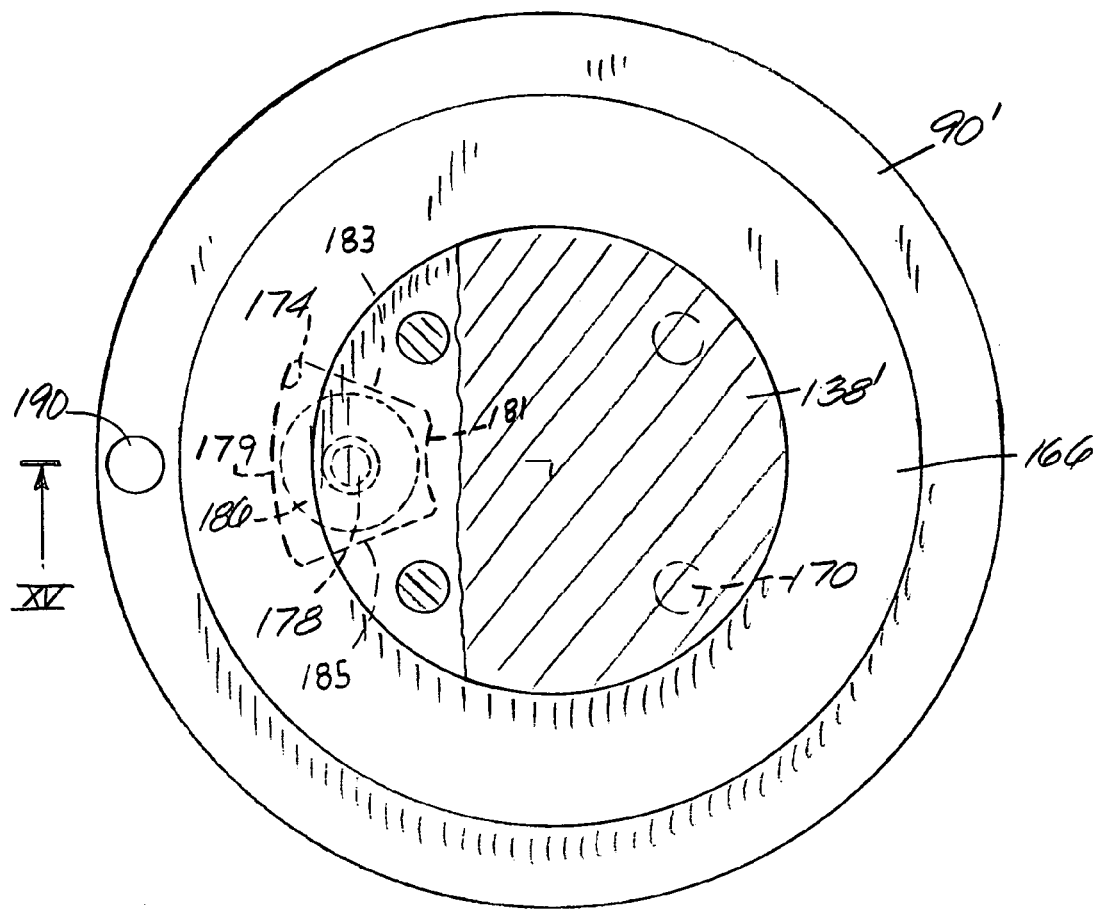
FIG. 15 is a top view, in partial cross-section, of a modified LCPA and a modified ram according to another embodiment of the present invention.
Figure 16:
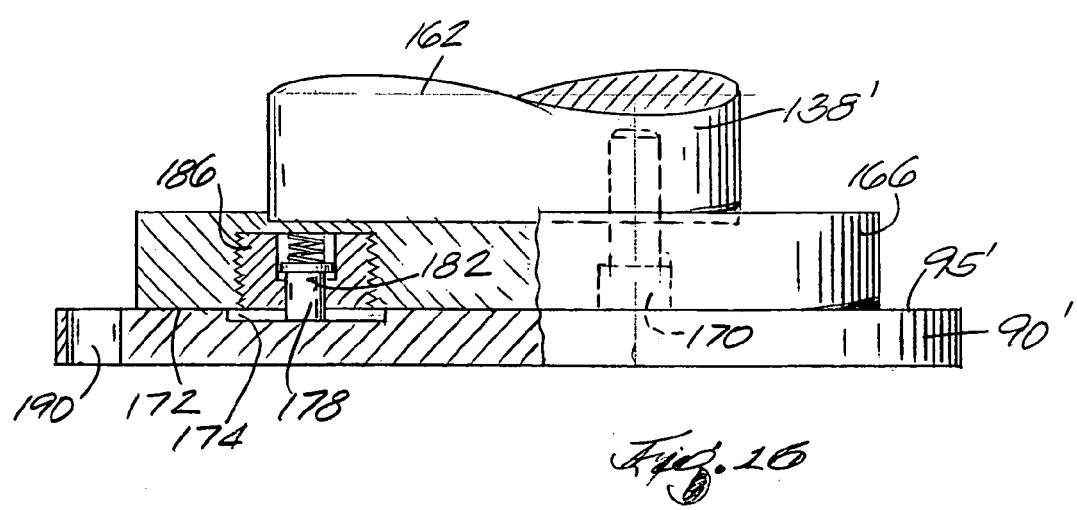
FIG. 16 is a partial cross-sectional view taken along line XV—XV of FIG. 15.

FIGS. 15 and 16 illustrate a modified LCPA and a modified ram. During the compaction and gyration process, it is possible that the outer plate may tend to slide with respect to the ram. Given the construction of a gyratory compactor, the electrical wires connecting the LCPA to a data acquisition system could be severed or damaged by the sliding action of the plate. Thus, it is desirable to substantially prevent the outer plate from sliding with respect to the ram during the testing process.

As shown in FIGS. 15 and 16, the ram 138' includes a shaft portion 162 and a base portion 166 which is connected to the shaft 162 by screws 170. The ram includes a planar surface 172 which abuts the outer surface 95' of the outer plate 90'. The outer surface 95' of th outer plate 90' includes a recess 174. A projecting member 178 extends from the planar surface 172 of the ram 138' into the recess 174 of the outer plate 90'. During the compaction and gyration process, the projecting member 178 engages the sides of th recess 174 to limit the movement of the outer plate 90' with respect to the ram 138'. Preferably, the recess is a quadrilateral having a pair of opposite sides 179 and 181 which are concentric with the plate 90', and a pair of opposite sides 183 and 185 which extend along radial lines of the plate 90'. In this way, when the projecting member 178 engages one of the radially extending sides, there are not any significant forces extending in the radial direction. If such forces were present, it is possible that the mold or machine would be damaged by virtue of the operation of the gyratory compactor. The projecting member 178 is preferably a spring loaded pin 182 which is placed within a cap 186 located in the base 166 of the ram 138'. A wire hole 190 may be provided in the outer plate so that the wires extending between the LCPA 82 and the data acquisition system 78 pass through the hole 190. The outer plate may be engageable with the ram in alternative ways, so long as the movement of the plate with respect to the ram is limited and so long as the forces generated between the outer plate and the ram do not cause significant damage to the mold or gyratory compactor itself.

The LCPA according to the present invention measures the overall frictional shear resistance of paving material specimens. The LCPA measures the distribution of stresses on the surface of the specimen thereby enabling the calculation of the effective moment required to shear the specimen. The effective moment can be used to calculate the overall frictional resistance of the mixture specimens. It was determined that the derived frictional resistance is sensitive to the asphalt content, aggregate gradation, and aggregate angularity.

The results according to the present invention indicate that the LCPA is an efficient and economical tool that has the potential to provide important information about frictional shear resistance and stability of asphalt mixtures. The data collected according to the present invention indicates that the correlation between volumetric properties and frictional shear resistance is not very strong. Some mixtures are fairly stable at the range of 2%–6% air voids while others are only in a transition zone, which is followed by a substantial loss of stability. This information could be vital in selecting a successful mixture design.

Variations and modifications of the foregoing are within the scope of the present invention. For example, the apparatus and method according to the present invention may be used to test materials, particularly paving materials, other than asphalt and asphalt aggregates. The apparatus and method according to the present invention may also be used in other testing devices which perform applied force testing. The embodiments described herein explain the best modes known for practicing the invention and will enable others skilled in the art to utilize the invention. The claims are to be construed to include alternative embodiments to the extent permitted by the prior art.

Various features of the invention are set forth in the following claims.

What is claimed is:

1. An apparatus for measuring a load applied to a quantity of material, said apparatus comprising:
    an inner plate having an inner surface and an outer surface, said inner surface of said inner plate being positionable against a portion of the quantity of material;
    an outer plate having an inner surface and an outer surface, said outer plate being spaced apart from said inner plate such that said inner surface of said outer plate is opposite said outer surface of said inner plate; and
    a vertically mounted load cell assembly comprising at least three load cells, each load cell comprising an upper portion and a load pin, wherein the upper portion of the load cell is connected to the outer plate and the load pin of the load cell contacts the outer surface of the inner plate, and wherein the load cells are substantially evenly spaced apart, such that said load cell assembly measures the load applied to the quantity of material when a force is exerted against the outer surface of said outer plate.

2. A gyratory compactor apparatus comprising:
    a frame;
    a mold supported by said frame, said mold having a cavity for receiving a quantity of material;
    an inner plate being positionable against a portion of the material;
    an outer plate which is spaced apart from said inner plate;
    a load cell assembly positioned between said inner plate and said outer plate for measuring a load, wherein the load cell assembly includes at least three load cells, wherein the load cells are substantially evenly spaced apart;
    a ram which is engageable with said outer plate and which is for compacting the material within said mold; and
    a mold gyrator for gyrating said mold as said ram compacts the material, such that said load cell assembly measures the load applied to the material when said ram exerts a force against said outer plate.

3. An apparatus according to claim 2, wherein said mold is a cylindrical mold, and wherein said inner plate is circular and has a first diameter and said outer plate is circular and has a second diameter which is slightly smaller than said first diameter.

4. An apparatus according to claim 2, wherein said outer plate is substantially prevented from sliding with respect to said ram when said mold gyrator gyrates said mold as said ram compacts the material.

5. An apparatus according to claim 4, wherein said ram includes a planar surface which abuts said outer surface of said outer plate when said ram compacts the material, wherein said outer surface of said outer plate includes a recess, and wherein said apparatus further includes:
    a projecting member which extends from said planar surface of said ram into said recess of said outer plate such that said projecting member is engageable with sides of said recess.

6. An apparatus according to claim 2, further comprising:
    a data acquisition system which is electrically coupled to said load cell assembly to record the load measurements taken by said load cell assembly; and
    a microprocessor which is electrically coupled to said data acquisition system to process and manipulate the recorded load measurements and volumetric properties.

7. An apparatus according to claim 6, wherein said second plate includes a hole therethrough to receive electrical wires connecting said data acquisition system to said load cell assembly.

8. A gyratory compactor comprising:
    a frame;
    a cylindrical mold supported by said frame, said mold having a cavity for receiving a paving material specimen;
    a circular inner plate having a first diameter, said inner plate being positionable against the specimen;
    a circular outer plate having a second diameter which is slightly smaller than said first diameter, said outer plate being spaced apart from said inner plate;
    a load cell assembly positioned between said inner plate and said outer plate for measuring a load, said load cell assembly having at least three load cells which are substantially evenly spaced apart;
    a ram which is engageable with said outer plate and which is for compacting the specimen within said mold;
    a mold gyrator for gyrating said mold as said ram compacts the specimen, such that said load cell assembly measures the load applied to the specimen when said ram exerts a force against said outer plate, and such that said outer plate is substantially prevented from sliding with respect to said ram when said mold gyrator gyrates said mold as said ram compacts the specimen;
    a data acquisition system which is electrically coupled to said load cell assembly to record the load measurements taken by said load cell assembly; and
    a microprocessor which is electrically coupled to said data acquisition system to interpret the recorded load measurements.

9. The apparatus of claim 2, wherein the microprocessor is electrically coupled to said gyratory compactor to process and manipulate the recorded load measurements and volumetric properties.

10. An apparatus for calculating a location of a resultant force, said apparatus comprising:
    an inner plate having an inner surface and an outer surface, said inner surface of said inner plate being positionable against a portion of the quantity of material;
    an outer plate having an inner surface and an outer surface, said outer plate being spaced apart from said inner plate such that said inner surface of said outer plate is opposite said outer surface of said inner plate; and
    a vertically mounted load cell assembly comprising at least three load cells, each load cell comprising an upper portion and a load pin, wherein the upper portion of the load cell is connected to the outer plate and the load pin of the load cell contacts the outer surface of the inner plate, and wherein the load cells are substantially evenly spaced apart, such that said load cell assembly measures a combined resultant force to the quantity of material when a force is exerted against the outer surface of said outer plate.

* * * * *